United States Patent [19]

Kauvar

[11] Patent Number: 5,356,784
[45] Date of Patent: Oct. 18, 1994

[54] DETERMINATION OF CONCENTRATION BY AFFINITY TITRATION

[75] Inventor: Lawrence M. Kauvar, San Francisco, Calif.

[73] Assignee: Terrapin Technologies, Inc., South San Francisco, Calif.

[21] Appl. No.: 39,786

[22] Filed: Mar. 30, 1993

[51] Int. Cl.$^5$ .................. G01N 33/53; G01N 33/543
[52] U.S. Cl. .................. 435/7.9; 435/7.92; 435/7.93; 435/810; 435/970; 435/300; 435/301
[58] Field of Search .................. 435/7.9, 7.92, 7.93, 435/810, 970, 300, 301; 422/56, 68.1

[56] References Cited

U.S. PATENT DOCUMENTS

| | | | |
|---|---|---|---|
| 4,618,475 | 10/1986 | Wang | 422/56 |
| 4,963,263 | 10/1990 | Kauvar | 210/635 |
| 5,133,866 | 7/1992 | Kauvar | 210/635 |
| 5,217,869 | 6/1993 | Kauvar | 435/7.9 |

OTHER PUBLICATIONS

De Jong, et al., *Biochemistry* 26 (7) 2039–2046, 1987.
Newport, et al., *J. Mol. Biol.* 145 (1) 105–122, 1981.
MacDonald, et al., *J. Immunol.* Methods 106 (2) 191–194, 1988.
*Practice and Theory of Immunoassays*, Elsevier Science Publishers, Amsterdam, The Netherlands, pp. 126–132, 1985.

*Primary Examiner*—Toni R. Scheiner
*Attorney, Agent, or Firm*—Morrison & Foerster

[57] ABSTRACT

A method for determining the amount of analyte in a sample utilizes a series of test regions with systematically varied, preferably monotonically increasing, affinity for a specific binding partner for an analyte or for the analyte itself. By determining the portion of test regions which are capable of binding specific binding partner in competition with the analyte in the sample, or which bind the analyte, the amount of analyte may be estimated. Thus, titration of affinity replaces titration of concentration, allowing assays to, be performed without the need for serial dilution steps.

20 Claims, 1 Drawing Sheet

FIG. IA
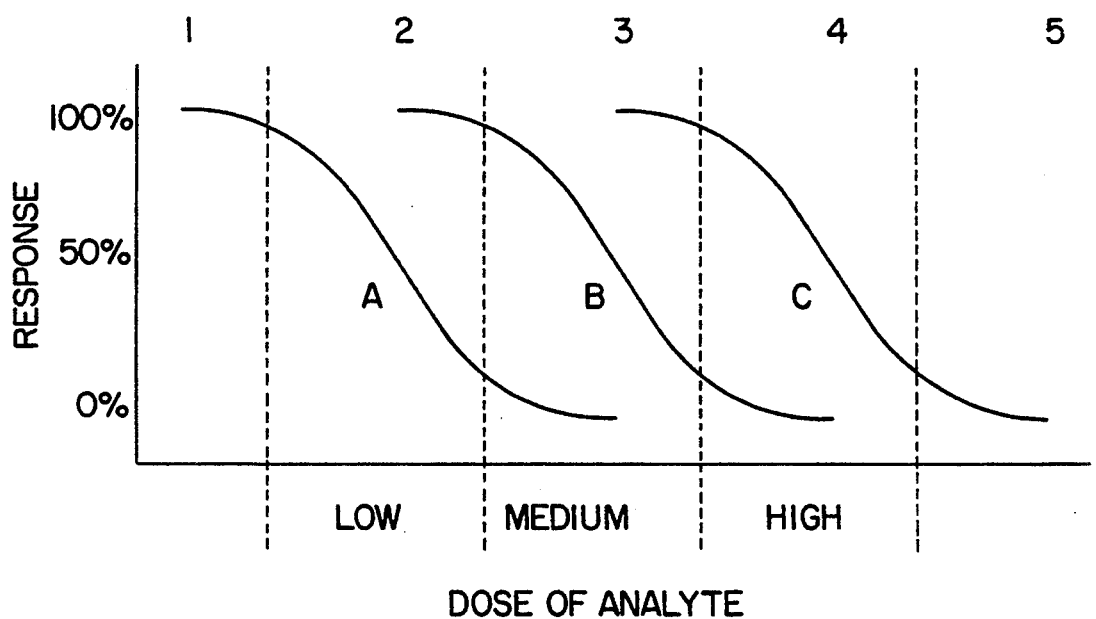
FIG. IB
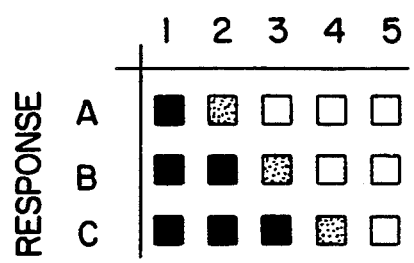

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Met  Tyr  Trp  Tyr  Pro  Tyr
    1                        5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Val  Gly  Arg  Ala  Phe  Ser
    1                        5

DETERMINATION OF CONCENTRATION BY AFFINITY TITRATION

FIELD OF THE INVENTION

The invention is related to determination of concentration of an analyte in a simplified, field-usable form suitable for use with small sample volumes. More specifically, the invention concerns use of a systematically variable competition immunoassay to determine concentration without the necessity for serial dilution, either to place the concentration of analyze within the ~1.5 log-unit range of a typical immunoassay or to obtain multiple readings in the dynamic range.

BACKGROUND ART

Assays to determine the concentration of analyte in clinical, environmental, or other settings generally involve the use of serial dilution. The purpose of such dilution is twofold: it may be necessary to bring the concentration of the sample within the range of the assay; if the sample is too concentrated, a meaningful reading may not result. Additionally, serial dilution may accommodate and span a dynamic range wherein variable readings over a series of concentrations is obtained, thus enhancing the precision of the result. In other cases, the level of dilution itself may be used as an assessment of concentration. In this instance, immunoassays or other specific binding assays can be used to assess the quantity of an analyte in a sample by using a multiplicity of test regions or portions in combination with serial dilutions of the sample. A variety of test formats is used wherein the same test format is used in these multiple test regions, but the sample containing analyte is used in lower and lower concentrations until a discernible response disappears. By taking account of the level of dilution at which a response is no longer visible, and comparing the results to those obtained with standards, the concentration of analyte in the original sample can be back-calculated.

Methods that employ serial dilution are useful, but quite labor- or machine-intensive, and are not suited for semiquantitative determinations as might be needed in testing for analytes outside of a laboratory context. For example, ascertaining the levels of contaminants in soil at the location where field testing is appropriate should be accomplished by methods that require only the application of a single sample volume, rather than the more complex and error-prone process of obtaining multiple dilutions. Similarly, in clinical settings, shortages of trained and reliable personnel manually to conduct serial dilutions for assessment is a recognized problem in supplying health care; instrumentation to make such dilutions mechanically is expensive and of limited reliability. Furthermore, it would be desirable to conduct clinical assays on extremely small samples so as to minimize the invasive nature of sample taking. Conduct of serial dilution on samples in the microliter range, for example, is inherently inaccurate.

One approach to this problem has been set forth in U.S. Pat. Nos. 4,654,310 and 4,923,800 to Ly. In the methods described, systematically varying amounts of test reagents in multiple test portions are used to obtain semiquantitative results for the same solution of analyte without necessity for serial dilutions of the sample. One easily understood disclosed approach takes advantage of two competing catalytically controlled reactions using varying relative amounts of the two catalysts. In its simplest form, two enzymes which utilize the analyte as the substrate compete for conversion of the substrate to product. One of the products gives an all-or-none detectable result; the other does not give a detectable response. If there is a high concentration of analyte, even large amounts of competing enzyme which take away from conversion to the detectable product don't matter; however, at low concentrations of analyte, not enough will be left to see the result. Therefore, high concentrations of analyte will be capable of giving a detectable result in the presence even of high concentrations of the competing enzyme; low concentrations of analyte will only give a detectable result at low concentrations of competing enzyme. In a somewhat different, but related, approach, described in U.S. Pat. 4,042,329 to Hochstrasser, variable stoichiometric reagent concentrations are used to achieve semiquantitative results in a series of test regions.

The present invention similarly provides a method that permits quantitative analyte concentration determination using a series of test regions without the need for serial dilution. In contrast to the abovementioned techniques, the invention method takes advantage of the variable binding affinity of a multiplicity of ligands either with the analyte itself or with a specific binding partner of the analyte. In either case, the invention takes advantage of a multiplicity of ligands which react with varying degrees of efficacy for a single substance.

DISCLOSURE OF THE INVENTION

The invention provides a method which is straightforward and quantitative for simple determination of the concentration of an analyte of interest under field or clinical conditions. The invention method takes advantage of varying affinities of ligands either for analyte or for a specific binding moiety, wherein the specific binding moiety is reactive with the analyte. In the preferred competitive mode, since the reagents offer varying degrees of competition for the specific binding partner, the competitive success of the test sample with regard to an orderly array of competitors can be used as an index of its amount following calibration runs with known concentrations of analyte.

Thus, in one preferred aspect, the invention is directed to a method to determine the quantity of an analyte in the sample, wherein the method comprises applying the sample to a multiplicity of test regions. The test regions contain ligands which have varying affinities for a specific binding partner that is capable of binding the desired analyte. The test regions are arranged sequentially—i.e., in such a manner that a monotonic increase of affinity of the contained ligands for the specific binding partner can be discerned. Of course, this is preferably done in the simplest possible way—e.g., in a linear arrangement wherein ligands of increasing affinity are arranged, for example, from left to right.

At the time the sample is contacted with the multiplicity of test regions, a quantity of specific binding partner is also supplied to each, and, indeed, can be contained in each test region *ab initio*. After contact of the test regions with the sample in the presence of specific binding partner, the specific binding partner that is not bound to the ligand coupled to the test region is washed away, if necessary. As is known in the art, for some methods of detection, washing is not necessary. The remaining bound specific binding partner is then detected. The portion of test regions containing bound specific binding partner is then used as a measure of the analyte. Intermediate values between all-or-none in each zone provide further precision in quantitation.

Unlike the semiquantitative data available from conducting the methods of Ly and Hochstrasser described above, the results obtained using the method of the present invention are susceptible to fully quantitative analysis if desired or can be interpreted more qualitatively. The precision of the answer obtained can be increased by augmenting the number of and appropriate selection of reagents for the test portions.

In the alternative, the multiplicity of test portions is used in a direct, noncompetitive format wherein the series of specific binding ligands are of varying affinities for the analyte itself. At low concentrations of analyte, only those test portions which contain ligands with high affinities for the analyte will bind sufficient amounts of analyte to be detectable. This form of the method of the invention can be conducted either in a kinetically controlled or equilibriumcontrolled format. The optimization of the range of binding affinities required to provide quantitative results will be different from that of the competitive format and can be conducted using routine experimentation.

In other aspects, the invention is directed to test devices for use in the method of the invention. These test devices contain a multiplicity of test regions containing ligands of varying affinity for the specific binding partner (or, with respect to the second format, for the analyte); the test regions are arranged in such a manner that regions containing ligands of increasing affinity for the specific binding partner (or analyte) can readily be discerned.

BRIEF DESCRIPTION OF DRAWINGS

FIG. 1 shows illustrative affinity titration curves for various reagents reactive with an analyte.

MODES OF CARRYING OUT THE INVENTION

In the invention method, titration of affinity replaces titration of concentration for generating a readable signal. The general principle can be described as follows: FIG. 1 illustrates three specific binding agents or ligands (A, B and C) for which the response to different doses of analyte are offset due to differential affinity of the binding agent for the analyte or for a competitor species. As shown, the displaced doseresponse curves generate a distinguishable response pattern for different concentration zones (numbered 1-5) of analyte. The concentration zone of an unknown specimen can thus be determined by comparing its response pattern with respect to these three ligands and comparing this response to that of standards. Quantitation within a zone can be accomplished by standard methods, if desired, or by increasing the number of different binding agents within this range.

U.S. Pat. 5,133,866, which is incorporated herein by reference, describes the production of diverse panels of ligands with maximally varying characteristics. These panels are particularly useful in supplying ligands of varying affinity for a single moiety, including a specific binding partner for analyte or for the analyte itself. While maximal diversity is not required for the ligands used in the present invention, such diversity is advantageous since it permits systematic control of the binding of the ligands for the analyte or specific binding partner.

While the diverse panels of ligands described in the above-referenced patent are a preferred source of the ligands with monotonically varying binding capability, other sources of such ligands could also be used. A series of monoclonal antibodies of varying affinities for their specific binding partner, for example, could be used. Similarly, peptides having random or systematically varied sequences can be generated using techniques by now well known in the art.

While it is relatively inconvenient to do so, it is not impossible to obtain a range of ligands of varying affinities essentially by trial and error among suitable candidates based on the nature of the target to which the ligand is to be bound. For example, if the analyte or the specific binding partner for analyte is an enzyme, variations on the substrate molecule or inhibitor molecules for the enzyme may be used. If the analyte or the specific binding partner for analyte is a receptor, variations on the ligand known to bind to the receptor might be used; conversely, if the target compound is a moiety which is known to bind to a receptor, variations in the binding site of the receptor protein can be employed.

Thus, a multiplicity of approaches for obtaining the desired collection of ligands with systematically varying affinities for analyte or specific binding partner for analyte is available in the art.

The preferred competitive form of the method uses a "specific binding partner" for analyte. As used herein, "specific binding partner" refers to a substance which is known to bind with considerable affinity for the desired analyte; typical such specific binding partners would be antibodies or immunologically reactive fragments thereof, such as Fab, Fab' or Fab'$_2$ fragments or, for example, when the analyte is a ligand which matches a receptor, the receptor for the ligand, etc. In addition, of course, if the analyte is itself an antibody, the specific binding partner can be the antigen to which the antibody is responsive.

The assay of the invention is preferably conducted on a solid support matrix to which the ligands of varying affinity for the specific binding partner or analyte are coupled. However, it would also be possible to format the assay for homogeneous solutions, e.g. a fluorescent energy transfer as a detection method is available in a homogeneous solution phase; no wash or attachment to solid support is required. The solid matrix may be of any design, so long as discrete test regions can be defined at its surface. Conventional substrates of this type, such as, for example, microtiter plates, can conveniently be used. Alternatively, flat, hydrophilic surfaces that have been divided into test regions by application of hydrophobic boundaries can be used. For example, a cellulose backing with wax crosshatchings so as to define a multiplicity of rectangular or square regions arranged linearly could be used. The design of the array of test regions is a matter of convenience and simplicity of interpreting the results. Preferably, the regions are arranged in such a manner that a linear array of ligands of increasing affinity for the specific binding partner or analyte can be coupled to the backing. Alternatively, the ligands can be arranged as a circle or a spiral or any other convenient, orderly design pattern. A multiplicity of a series of such ligands of monotonically increasing affinity for specific binding partners of the same analyte or different analytes can be arranged on the surface of the same substrate or solid support.

The nature of the coupling of the individual ligands to the test regions, if such coupling is desired, also varies widely, depending on the nature of the solid substrate and the nature of the ligand used. The binding may be covalent or by adsorption. If peptides are used as a source of ligands having multiple affinities, linker moieties capable of forming ester, amide, or disulfide bonds with the peptide and suitable covalent bonds with the substrate may be employed. However, additional types of ligands, including nucleic acids, carbohydrates, and other polymers could also be used. Some of these are described in the above-referenced patent. Coupling is through conventional procedures; for example, binding to cellulose substrates may be effected by cyanogen bromide, alkyl chloroformares or carbonyl diimidazole to form cyclic carbonate or carbonate active esters.

In setting up the test device, each test region is separately coupled to the ligand of specified affinity in a known pattern. The coupling thus results in a series of test regions of varying affinity for the specific binding partner or analyte.

For conduct in the competition format, the support containing the test regions may optionally be supplied with a known, preferably constant, amount of specific binding partner contained in, but not coupled to, each test region in advance of the test itself. Alternatively, the specific binding partner may be supplied as a separate solution at the time sample is applied. In the conduct of the test, the sample is applied to the entire series of test regions along with a constant amount of specific binding partner. The sample and specific binding partner are allowed to remain in contact with the series of test regions for sufficient time to permit competition for the specific binding partner between the ligand and the analyte contained in the sample. Depending on the method of detection of binding of specific binding partners to the ligand, it may or may not be necessary or desirable, after the incubation period, to wash the test portions so that only specific binding partner bound to ligand in the test region remains.

In any event, the presence or absence of ligand-bound specific binding partner in a specific test region is detected after incubation in competition with the sample containing analyte. This detection can be conducted in a variety of ways. In some methods, it is not necessary to wash away solution containing unbound specific binding partner. For example, in a format involving coupling of ligand to solid support, the solid support may be provided with a fluorescence-emitting compound wherein the fluorescence can be quenched by a moiety attached to the specific binding partner. Only bound specific binding partner is capable of quenching the fluorescence, and the presence of unbound partner in the solution does not interfere with the reading. This method can also be used in homogeneous medium where the ligand is in solution in the test region. Alternatively, optical devices which detect the presence or absence of a signal, such as a fluorescence signal, only at the surface and not elsewhere can also be employed.

More traditional methods, such as, for example, adding a substrate solution to the series of test regions wherein the specific binding partner is coupled to an enzyme for the detection of bound enzyme may require prewashing of the test regions. If the test regions are, indeed, washed free of unbound specific binding partner, the presence or absence of the specific binding partner is then detected for each test region using such conventional methods. For example, if the specific binding partner is an antibody, this antibody may itself contain a label or may be labeled using a second antibody specifically immunoreactive with it. Various conventional methods of labeling are well known in the art, including radiolabeling, enzymatic labeling, fluorescent labeling, and combinations of these.

When detection has been effected, the pattern of binding is then observed. In a single series of test regions, samples with large concentrations of analyte will result in failure to bind specific binding partner in the majority of test regions. Samples containing only low amounts of analyte which are poorly capable of competing with coupled ligand will result in a series wherein most of the test regions show the presence of label. Thus, the proportion of test regions showing binding is roughly inversely proportional to the level of analyte in the sample. The test is made semiquantitative by suitable standardization with known amounts of analyte.

The level of precision may be varied according to the desired need for same by adjusting the relative affinities of the test portions for the specific binding partner. A large number of such test portions having ligands with only moderate increments of affinity can be used to enhance the precision of the assay.

Alternatively, in the direct format, the multiplicity of test portions is contacted with the sample putatively containing analyte. The ability of the analyte to bind to ligand in a particular test portion will depend on the affinity of the ligand residing in that test portion for the analyte itself. Binding can be judged on a kinetic or equilibrium basis; if judged on a kinetic basis, short-term incubations which terminate prior to establishment of equilibrium are used.

In this format, analyte will bind to ligand in those test portions containing ligand for which it has the highest affinity preferentially; at low concentrations, only test portions having ligands with very high affinity for the analyte will succeed in binding detectable amounts of analyte. At higher concentrations of analyte even test portions with ligand having relatively small affinities will be able to bind analyte.

The detection of ligand-bound analyte in this format may also be conducted by measuring changes in characteristics of the surface of the solid support due to binding; however, more conventional approaches involving removing sample containing unbound analyte and then using a secondary binding agent containing label are preferred. Washing, however, is generally not indicated since this may alter the binding characteristic of the sample. One example of this approach would employ, for example, an antibody or fragment thereof capable of specifically binding analyte wherein the antibody or fragment itself contains a radioactive, fluorescent, enzyme, or other label.

The results are then read by comparing the number of test regions binding analyte in standard concentration controls as compared to the number of regions binding analyte in the sample to be tested. In this format, higher concentrations of analyte will show detectable binding in a greater number of test regions.

Whether conducted in a direct or competitive format, the assay is conducted using a multiplicity of test regions. Preferably, the test regions are arranged in such a way that the result in each can be measured and associated with a particular ligand. For direct reading devices, some orderly arrangement will be necessary, such as a linear arrangement of ligands with increasing affinity for analyte or increasing affinity for the specific binding reagent. Alternatively, other orderly arrangements such as spirals or even two-dimensional arrays could be used, as long as the results are intelligible. If the test regions are simply wells of a microtiter plate or test tubes in a rack, the arrangement is flexible and at the option of the practitioner. Random physical arrangements may also be used using computer processing to sort out the position of the ligands of various affinities. In principle, however, in a single formated test, simply the number of test portions which provide positive results will be determinative.

One particularly convenient method to construct a device with the required number of test regions comprises a basic hydrophilic matrix wherein regions of the matrix are separated from each other by hydrophobic barriers. Thus, a cellulose mat might be subdivided into squares or other suitably shaped regions by lines of wax or other hydrophobic barrier.

The following example is intended to illustrate but not to limit the invention.

The invention can be illustrated using materials described by Scott, J. K. et al. *Proc Natl Acad Sci USA* (1992) 89:5398-5402. Briefly, the lectin Concanavalin A (ConA) specifically binds the sugar methyl-alpha-Man (MeMan). Multivalent ConA can also bind various bacterial-derived dextrans such as that from strain B-1355-5, to form an insoluble complex. Precipitation of ConA-dextran can be inhibited in a dosedependent manner by MeMan.

By screening a phage epitope display library, several peptides (e.g. MYWYPY (SEQ ID NO: 1) and VGRAFS (SEQ ID NO: 2) were identified which also inhibit Con A-dextran precipitation, with distinctive 50% inhibition values.

Measurement of MeMan as an analyte can thus in principle be accomplished using peptides as competing ligands or for blocking the precipitation of ConAdextran, effectively expanding the range of MeMan concentrations that can be measured. Dextran and peptides could also in principle be immobilized and used to trap ConA competitively with MeMan. Conversely, Con A could be viewed as the analyte and dextran B-1355-5 as the specific binding agent, with MeMan and the peptides as competing agents that allow a range of ConA concentrations to be determined.

---

---

I claim:

1. A method to determine the concentration of an analyte in a sample, which method comprises:
   (a) applying said sample to a multiplicity of test regions, which contain a series of ligands of systematically varying affinity for a specific binding partner, wherein said specific binding partner specifically binds said analyte, wherein said test regions are arranged in a pattern to permit orderly retrieval of test results in each test region, and wherein said applying is conducted in the presence of a constant amount of said specific binding partner, under conditions wherein said ligand and said analyte compete for said specific binding partner;
   (b) detecting said specific binding partner bound to the ligand in each test region; and
   (c) determining the concentration of analyte by determining the number of test regions to which specific binding partner is bound and comparing said number to the number that would be bound by a known concentration of analyte.

2. The method of claim 1 wherein said ligands are coupled to a solid support.

3. The method of claim 1 which further includes, after step (a), the step of removing specific binding partner that is not bound to the ligand contained in each test region.

4. The method of claim 1 wherein said ligands are polymers having diverse characteristics with respect to at least two parameters selected from the group consisting of hydrophobicity, charge distribution, and corrugation factor.

5. The method of claim 1 wherein said bound specific binding partner is labelled with an enzyme or radioactive label.

6. The method of claim 1 wherein said bound specific binding partner is detected by assessing a difference in a characteristic of the test region.

7. The method of claim 6 wherein said characteristic is fluorescence.

8. The method of claim 2 wherein said test regions are arranged linearly on a planar surface as a series of hydrophilic matrices separated by hydrophobic barriers.

9. The method of claim 1 wherein said test regions further contain said specific binding partner.

10. The method of claim 1 wherein said specific binding partner is an antibody or immunologically reactive fragment thereof.

11. The method of claim 10 wherein said antibody or fragment further contains an enzyme or radioactive label.

12. The method of claim 1 wherein said test regions are arranged sequentially with ligands of systematically increasing affinity for said specific binding partner.

13. A method to determine the concentration of an analyte in a sample, which method comprises:
(a) applying said sample to a multiplicity of test regions which contain a series of ligands of systematically varying affinity for said analyte, wherein said test regions are arranged in a pattern to permit orderly retrieval of the results in each test region;
(b) detecting any said analyte bound to ligand in each test region; and
(c) determining the concentration of analyte by determining the number of test regions to which analyte is bound and comparing said number to the number that would be bound by a known concentration analyte.

14. The method of claim 13 wherein said ligands are coupled to a solid support.

15. The method of claim 13 which further includes, after step (a), the step of removing analyte that is not bound to the ligand contained in the test region.

16. The method of claim 13 wherein said ligands are polymers having diverse characteristics with respect to at least two parameters selected from the group consisting of hydrophobicity, charge distribution, and corrugation factor.

17. The method of claim 13 wherein said bound analyte is detected by assessing a difference in a characteristic of the test region.

18. The method of claim 17 wherein said characteristic is fluorescence.

19. The method of claim 14 wherein said test regions are arranged linearly on a planar surface as a series of hydrophilic matrices and separated by hydrophobic barriers.

20. The method of claim 13 wherein said test regions are arranged sequentially with ligands of systematically increasing affinity for said analyte.

* * * * *